US008853195B2

(12) United States Patent  (10) Patent No.: US 8,853,195 B2
Choi  (45) Date of Patent: Oct. 7, 2014

(54) COMPOSITION FOR REDUCING THE EXUDATION OF SERUM PROTEINS

(75) Inventor: Seong-hyun Choi, Gangwon-do (KR)

(73) Assignee: KT & G Corporation (KR)

( * ) Notice: Subject to any disclaimer, the term of this patent is extended or adjusted under 35 U.S.C. 154(b) by 190 days.

(21) Appl. No.: 11/885,028

(22) PCT Filed: Feb. 23, 2006

(86) PCT No.: PCT/KR2006/000638
§ 371 (c)(1),
(2), (4) Date: May 6, 2008

(87) PCT Pub. No.: WO2006/091033
PCT Pub. Date: Aug. 31, 2006

(65) Prior Publication Data
US 2009/0029950 A1  Jan. 29, 2009

(30) Foreign Application Priority Data
Feb. 28, 2005 (KR) .................. 10-2005-0016567

(51) Int. Cl.
A01N 43/00 (2006.01)
A61K 31/33 (2006.01)
A61Q 19/00 (2006.01)
A61K 9/00 (2006.01)
A61K 8/55 (2006.01)
A61K 31/683 (2006.01)
A61K 31/685 (2006.01)
A61K 47/10 (2006.01)

(52) U.S. Cl.
CPC ............. *A61K 8/553* (2013.01); *A61Q 19/00* (2013.01); *A61K 9/0014* (2013.01); *A61K 31/683* (2013.01); *A61K 31/685* (2013.01); *A61K 9/007* (2013.01); *A61K 47/10* (2013.01)
USPC ......................... 514/183; 514/120

(58) Field of Classification Search
None
See application file for complete search history.

(56) References Cited

U.S. PATENT DOCUMENTS

| | | | | |
|---|---|---|---|---|
| 5,698,537 A * | 12/1997 | Pruss | ................ | 514/78 |
| 6,228,891 B1 | 5/2001 | Enzmann et al. | | |
| 6,320,017 B1 * | 11/2001 | Ansell | ............ | 528/310 |
| 6,770,619 B2 | 8/2004 | Larsson et al. | | |
| 2002/0037316 A1 * | 3/2002 | Weers et al. | ................... | 424/450 |
| 2003/0044357 A1 | 3/2003 | Hills et al. | | |
| 2004/0009216 A1 | 1/2004 | Rodrigueza et al. | | |
| 2004/0228910 A1 | 11/2004 | Enzmann et al. | | |
| 2005/0080052 A1 | 4/2005 | Hills et al. | | |
| 2009/0029950 A1 | 1/2009 | Choi | | |

FOREIGN PATENT DOCUMENTS

| | | |
|---|---|---|
| CN | 1560057 A | 1/2005 |
| EP | 0 528 034 B1 | 2/1993 |
| JP | S624215 A | 1/1987 |
| JP | S62209010 A | 9/1987 |
| JP | 2078432 A | 3/1990 |
| JP | 11-130615 A | 5/1999 |
| JP | 2002-530344 A | 9/2002 |
| JP | 2004131401 A | 4/2004 |
| JP | 2004-231544 A | 8/2004 |
| JP | 2004352643 A | 12/2004 |
| JP | 5074929 B2 | 11/2012 |
| KR | 10-1998-0700061 A | 3/1998 |
| KR | 10-2005-0009988 A | 1/2005 |
| RU | 2157222 C2 | 10/2000 |
| RU | 2198670 C1 | 2/2003 |
| WO | WO 91/17766 | 11/1991 |
| WO | 98/31346 A1 | 7/1998 |
| WO | WO 99/27920 | 6/1999 |
| WO | WO 99/30722 | 6/1999 |
| WO | 99/44582 A2 | 9/1999 |
| WO | 01/19392 A1 | 3/2001 |
| WO | WO 2004/110450 A1 | 12/2004 |
| WO | 2005004829 A1 | 1/2005 |
| WO | 2006-091033 A1 | 8/2006 |

OTHER PUBLICATIONS

Babu et al., "Inhaled synthetic surfactant abolishes the early allergen-induced response in asthma," European Respiratory Journal, 2003, pp. 1046-1049, vol. 21.
Chang et al., "The Relationship Between Inflammation and Dipalmitoyl Phosphatidycholine in Induced Sputum of Children with Asthma," Journal of Asthma, Feb. 2003, pp. 63-70, vol. 40, No. 1.
Cheng et al., "Increased levels of surfactant protein A and D in bronchoalveolar lavage fluids in patients with bronchial asthma," European Respiratory Journal, 2000, pp. 831-835, vol. 16.
Goerke, "Pulmonary surfactant: functions and molecular composition," Biochimica et Biophysica Acta 1408, 1998, pp. 79-89.
Hills et al., "Adsorption of Surfactant to Bronchial Epithelium: Possible Role of Receptor 'Unmasking' in Asthma," Journal of Asthma, Jun. 2003, pp. 445-450, vol. 40, No. 4.
Abstract of Li et al., "Protective and therapeutic effect of pulmonary surfactant on the experimental chronic obstructive pulmonary disease in hamsters," Zhongguo Yi Xue Ke Xue Yuan Xue Bao, Jun. 2004, pp. 279-284, vol. 26, No. 3.
Mallampalli et al., "Very Low Density Lipoproteins Stimulate Surfactant Lipid Synthesis in Vitro," The Journal of Clinical Investigation, Apr. 1997, pp. 2020-2029, vol. 99, No. 8.

(Continued)

*Primary Examiner* — Wu-Cheng Winston Shen
*Assistant Examiner* — Jean Cornet
(74) *Attorney, Agent, or Firm* — Lerner, David, Littenberg, Krumholz & Mentlik, LLP

(57) ABSTRACT

Disclosed is a composition for reducing the exudation of the serum proteins. More specifically the composition of the present invention relates to a composition capable of improving conditions such as atopic dermatitis, atopic eczema, skin pruritus, atopic nasitis, atopic erythema or erythroderma, contact dermatitis, asthma, chronic obstructive pulmonary disease, etc. by reducing the exudation of the serum proteins in skin and mucosa.

19 Claims, 4 Drawing Sheets

(56) References Cited

OTHER PUBLICATIONS

Veldhuizen et al., "The role of lipids in pulmonary surfactant," Biochimica et Biophysica Acta 1408, 1998, pp. 90-108.

Wang et al., "Inhibitory Effect of Pulmonary Surfactant Proteins A and D on Allergen-induced Lymphocyte Proliferation and Histamine Release in Children with Asthma," American Journal of Respiratory and Critical Care Medicine, Aug. 1998, pp. 510-518, vol. 158, No. 2.

International Search Report for PCT/KR2006/000638, date of mailing, Apr. 21, 2006, 3 pages.

Gehring et al., "Influence of topically applied ceramide/phospholipid mixture on the barrier function of intact skin, atopic skin and experimentally induced barrier damage", *International Journal of Cosmetic Science*, vol. 19, 1997 (pp. 143-156).

Korean Abstract of KR Patent Publication No. 10-2003-0053507 A, Jun. 28, 2003 (Abstract only).

Anzueto et al., "Effects of Aerosolized Surfactant in Patients With Stable Chronic Bronchitis", *JAMA*, vol. 278, No. 17, Nov. 5, 1997 (pp. 1426-1431).

Ikegami et al., "Corticosteroids and Surfactant Change Lung Function and Protein Leaks in the Lungs of Ventilated Premature Rabbits", *J. Clin. Invest.*, vol. 79, May 1987 (pp. 1371-1378).

Kurashima et al., "A Pilot Study of Surfactant Inhalation for the Treatment of Asthmatic Attack", *Jpn. J. Allergol.*, vol. 40, No. 2, 1991 (pp. 160-163).

Liu et al., "Pulmonary surfactant given prophylactically alleviates an asthma attack in guinea-pigs", *Clinical and Experimental Allergy*, vol. 26, 1996 (pp. 270-275).

Robertson et al., "Leakage of Protein in the Immature Rabbit Lung; Effect of Surfactant Replacement", *Respiration Physiology*, vol. 61, 1985 (pp. 265-276).

Supplementary European Search Report for Application No. EP 06 71 6088, date of completion of the search Jul. 24, 2008 (3 pgs.).

Wirtz et al., "Exogenous Surfactant Application in Respiratory Failure due to Chronic Obstructive Pulmonary Disease", *Respiration*, vol. 62, 1995 (pp. 157-159).

Hohlfeld, J. et al., "The role of pulmonary surfactant in obstructive airways disease," European Respiratory Journal, 10: pp. 482-491 (1997).

Phelps, D. S., "Surfactant Regulation of Host Defense Function in the Lung: A Question of Balance," Fetal and Pediatric Pathology, 20: 4, pp. 269-292 (2001).

Pison, U. et al., "Host defence capacities of pulmonary surfactant: evidence for 'non-surfactant' functions of the surfactant system," European Jrl. of Clinical Investigation, 24, pp. 586-599 (1994).

\* cited by examiner (Female, 6 years old) Before/after 4 weeks (Female, 6 years old) Before/after 5 weeks (Female, 16 years old) Before/after 3 weeks (Female, 0.8 years old) Before/after 3 weeks

COMPOSITION FOR REDUCING THE EXUDATION OF SERUM PROTEINS

TECHNICAL FIELD

The present invention relates to a composition for reducing the exudation of the serum proteins, and more specifically to a composition for improving the conditions such as atopic dermatitis, atopic eczema, skin pruritus, atopic nasitis (rhinitis), atopic erythema or erythroderma, contact dermatitis, asthma, chronic obstructive pulmonary disease, etc. by reducing the exudation of the serum proteins in skin and mucosa.

BACKGROUND ART

For the purpose of the academic understanding of atopic diseases and the improvement and the treatment of their symptoms, there are many attempts by researchers to understand the immunoregulatory mechanisms in a living body or the cell signaling mechanisms and the methods employing the mechanisms along with the development of immunology and cytology. On the other hand, some studies have been going on by some researchers to elucidate the causes of the diseases on the changes with the development of modern civilization, that is, the changes in diet or the exposure to pollutants.

The common fact found in the studies on the atopic diseases in these various findings is that the serum proteins exude from skin or mucosa of patients with atopic diseases, regardless of the understanding that the atopic diseases would be caused by the immunological reasons. However, there has been no study to conclude clearly whether the serum proteins exude from the skin or mucosa as a result of the development of the atopic diseases or the exudation of the serum proteins in the skin or mucosa triggers the atopic diseases.

It is known that the exudation of the serum proteins in outer skin or mucosa are observed mainly using serum albumin as a marker protein. It has been known that an exudation level of serum albumin in the skin diseases is closely correlated with the severity of the diseases. Hypoalbuminemia in the blood is induced as the serum proteins severely exuded from the skin (Worm et al., 1981. Br. J. Dermatol. 104: 389-396; and Worm and Rossing, 1980. J. Invest. Dermatol. 75: 302-305). Patients are suffering from allergic asthma and rhinitis developed symptoms such as intestinal lymphangiectasia that resulted by severe loss of albumin through the inner wall of the intestines (Esenberh, 1976. Ann. Allergy, 36: 342-350). In case of children, the loss of albumin by severe skin diseases makes them retard their growth (Abrahamov, 1986. Eur. J. Pediatr. 145: 223-226), and is also accompanied with oiguria and acrocyanosis along with the lymphangiectasia (Capulong et al. 1996. Pediatr. Allergy Immunol. 7: 100-102). It was reported that an exudation level of albumin in diseased skin area is closely related to the severity of the conditions even in the case of atopic eczema and contact dermatitis (David et al., 1990. Br. J. Dermatol. 122: 485-489; and Wijsbek et al., 1991. Int. J. Microcirc. Clin. Exp. 10: 193-204).

It was reported that the exudation of albumin-including serum proteins was found even in sputa of the patients suffering from symptoms of asthma and chronic obstructive pulmonary disease (Schoonbrood et al. 1994. Am. J. Respir. Crit. Care Med. 150:1519-1527; and Anderson & Persson 1988. Agents Actions Suppl. 23: 239-260), and it was also reported that the exudation of albumin occurs without a sign of eosinophilia in the case of chronic cough (Pizzichini et al., 1999. Can. Respir. J. 6:323-330).

The exudation of the serum proteins is induced by the chemicals including materials such as methyl salicylate, phenol, croton oil, benzalkonium, etc. (Patrick et al. 1985. Toxicol. Appl. Pharmacol. 81: 476-490); and toluene, m-xylene, cyclohexane, etc. (Iyadomi et al., 1998. Ind. Health 36:40-51). 2,4-dinitrofluorobenzne is used in the animal models to conduct a skin irritation study, and also induces the exudation of the serum proteins (Nakamura et al., 2001. Toxical. Pathol. 29:200-207). It was reported that all organic solvent materials do not induce the exudation of the serum proteins, and the exudation levels are also varied according to the structure of chemicals. The exudation of the serum proteins is easily induced by the chemicals having aromatic rings, but nearly affected by organic solvents such as acetone.

Keeping in mind that the atopic diseases are caused by reason of the westernized food habits (Weiland et al., 1999. Lancet 353:2040-2041; von Mutis et al., 1998. Lancet 351: 862-866; and Dunder et al., 2001. Allergy 56:425-428), the researchers have paid attention to the changes of the components and the content of lipids ingested by the people. With the advent of 1970s, a few of researchers have found that the imbalance of the human metabolism is caused by the excessive ingestion of unsaturated fatty acid and trans oil which are main components of vegetable oil, which results in the augmentation of the atopic diseases.

Unlike other tissues and organs, there are various phospholipids having a very high content of di-saturated fatty acids in lungs of mammals including human, and the surfactant present on the surface of lung have, in particular, a very high content of dipalmitoylphosphatidylcholine (DPPC). It has been known that the component functions to reduce a surface tension in lungs. The reduction of the surface tension by the surfactant on the surface of lung can be made easy to breathe when air is inhaled into the lungs, and prevents alveolar walls from being attached to each other or their structure from being collapsed when exhaled out. The lipid component of the surfactant is composed of about 90% of phospholipid (about 70% of the phospholipid is di-saturated phospholipid), and about 10% of neutral fat (a majority of the neutral fat is cholesterol) (Reviews: Jon Goerke 1998. Biochem. Biophy. Acta. 1408:79-89; and Veldhuizen et al., 1998. Biochim. Biophys. Acta. 90-108).

One of the scientific results that should be further considered in addition to the facts as described above is a pathway for synthesizing the surfactant lipids in the lungs. One point is that most cholesterol present in the human lung is supplied from the blood. Cholesterol synthesized in the lung accounts for only about 1%, and the rest of cholesterol should be supplied from the blood (Hass and Longmore, 1979. Biochim. Biophys. Acta 573:166-174). It has been known that phospholipids constituting most of the surfactant of the lung are synthesized in and secreted from Type II epithelial cells, but most of the fatty acid constituting the phospholipids are supplied from VLDL (very low density lipoprotein) in the blood (Rama et al., 1997. J. Clin. Invest. 99: 2020-2029).

SP-A (surfactant protein A) is one of the major proteins present in the surfactant in lung that has been studied for the last 30 years. The SP-A protein is synthesized in and secreted from Type II epithelial cells present in the alveoli, and also found in a surface of the small intestine, Eustachian tube of ear, tears, etc. Its molecular weight is approximately 700 kDa (measured by a gel-filtration assay), and its 18 identical units, each having a molecular weight of 32 kDa, are gathered to form a mature protein having the peculiar function. It has been known that the protein has various biological functions, but they may be mainly categorized into two groups. The first is an immunological function in which SP-A protects the lungs by binding to bacteria or viruses, as well as a house dust mite, anther dust, etc. which enter the lungs while breathing in. The second function is taking part in maintaining the homeostasis of the surfactant in lung (Tino and Wright 1998. Biochim. Biophys. Acta. 1408: 241-263; Haagsman, Biochim. Biophys. Acta. 1408: 264-277; Crouch & Wright, 2001. Annu. Rev. Physiol. 63:521-524; and Haagsman and Diemel, 2001 Compar. Biochem. Physiol. 129: 191-108).

DISCLOSURE OF INVENTION

Accordingly, the present invention is designed to solve the problems of the prior art, and therefore it is an object of the present invention to provide a composition for treating and/or relieving the diseases relevant to the exudation of the serum proteins.

In order to accomplish the above object, the present invention provides a composition for treating or relieving diseases relevant to the exudation of serum proteins, including di-saturated phospholipids as effective components.

The di-saturated phospholipids of the present invention are preferably extracted from animals, more preferably from cattle and pig, and the most preferably from their bronchial alveolar lavage or their lung tissue homogenates.

Also, the di-saturated phospholipids of the present invention are preferably dipalmitoylphosphatidylcholine and/or dipalmitoylphosphatidylinositol.

Also, the composition of the present invention preferably further includes calcium ions and an organic acid containing carboxyl group(s), and the organic acid including carboxyl group(s) preferably includes, but is not limited to, metabolizable organic acid, for example lactic acid, succinic acid, fumaric acid or citric acid. In addition, the composition of the present invention further may include additives, for example glycerol, if necessary. In the composition of the present invention, the di-saturated phospholipids are preferably present at a concentration of 1 to 700 mg/ml. The aforementioned concentration range is the most preferred since the di-saturated phospholipids exhibits a poor therapeutic or relaxation effect at a concentration of 1 mg/ml or less and is difficult to be used because a high viscosity of a suspension makes its homogenization impossible at a concentration of 700 mg/ml or more.

Also, the present invention provides a composition for treating skin diseases, containing the composition of the present invention. Also, the present invention provides a cosmetic composition containing the composition of the present invention.

The serum protein exudation-related diseases of the present invention includes, but is not limited to, diseases selected from the group consisting of atopic dermatitis, atopic eczema, skin pruritus, atopic nasitis, atopic erythema or erythroderma, contact dermatitis, asthma, and chronic obstructive pulmonary, etc.

Hereinafter, the present invention will be described in detail.

In the present invention, on the basis that the atopic diseases have a common symptom that the serum proteins exude from skin or mucosa because a function of an endothelial-epithelial barrier is lowered by excessive intake of unsaturated fatty acid and trans oil, a novel animal model was employed. It was found that, when saline-emulsified plant-extracted oil is intratracheally introduced into rat lung, the animal showed the exudation of the serum proteins in the lung. It is also found that the symptom of the exudation of the serum proteins can be reduced or suppressed by the intratracheal administration of the stable biocomponents—a composition invented here—that are completely metabolized in vivo. And, it is also found that the composition, containing the di-saturated phospholipids isolated from animal's lung, a certain concentration of calcium ions and organic acid which contains (a) carboxyl group(s), act successfully on the affected skin area of patients with the atopic diseases.

In the present invention, it has been found that a unique sedimentary layer containing an ideal combination of the di-saturated phospholipids is formed when the SP-A protein is aggregated in the presences of divalent cations and then spun in bronchial alveolar lavage or lung homogenate of the healthy animal. The present invention includes a method including the steps eliminating the surfactant proteins (especially, organic solvent-soluble proteins SP-B and SP-C) and hydrophobic peptides which may induce immune responses in human, cholesterol and unsaturated phospholipids from the sedimentary layer, and then obtaining an ideal combination of the di-saturated phospholipid fractions existing in healthy animal lung. On the basis of the findings that the SP-A protein exhibits a strong non-specific hydrophobic interaction in the absence of divalent cations, a certain concentration of calcium ions is required when a composition containing the di-saturated phospholipid fraction is applied to skin or mucosa of the patients with an atopic disease to suppress or to reduce the exudation of the serum proteins, as well as the organic acids having (a) carboxyl group(s) which can be metabolized in cell, for example citrate or citric acid are further added to the composition to prevent the di-saturated phospholipids from being aggregated by a certain concentration of calcium ions.

BRIEF DESCRIPTION OF THE DRAWINGS

These and other features, aspects, and advantages of preferred embodiments of the present invention will be more fully described in the following detailed description, taken accompanying drawings. In the drawings:

In FIG. 1, the * indicator represents the di-saturated phospholipid fraction.

In FIG. 2, Diagram 1 shows that the pulmonary protein profile from a rat in which the exudation of the serum proteins was induced by administrating saline-emulsified corn oil into the rat lung, Diagram 2 shows the pulmonary protein profile after the composition was administered into the rat which the exudation of the serum proteins was induced previously, and Diagram 3 shows the pulmonary protein profile from a control rat. "A" indicates a peak of the proteins containing an SP-A (approximately 700 kDa molecular weight), and "B" indicates a peak of the proteins containing serum albumin (approximately 70 kDa). A level of the suppression or reduction of the exudation of the serum proteins was assessed by comparing the sizes of two peaks, A and B.

BEST MODES FOR CARRYING OUT THE INVENTION

Hereinafter, the present invention will be described more in detail with reference to the preferred embodiments. However, it should be understood that the description proposed herein is just a preferable example for the purpose of illustrations only, not intended to limit the scope of the invention.

Example 1

Extraction of the Di-saturated Phospholipid Fraction from Bronchial Alveolar Lavage of Pig (1) A Method for Obtaining a Bronchial Alveolar Lavage Lung taken from a healthy pig was lavaged by administering an osmotic saline solution, containing 5 mM calcium chloride ($CaCl_2$), into the lung. The lavaging was carried out at a room temperature by administering about 0.6 L. of a solution to one of the lungs using a pressure pump, followed by collecting a lavage that exudes from the lung. The lavaging was carried out with 15 L of a saline solution per lung. The collected bronchial alveolar lavage was immediately transferred to an ice-water bath and cooled down.

(2) A Method for Obtaining a Precipitate of the Surfactant from a Bronchial Alveolar Lavage Using an Aggregation Phenomenon.

As the bronchial alveolar lavage including calcium ion (5 mM) was kept in an ice-water bath for 1 hour, then the SP-A protein begins to aggregates with the lipids in the surfactant. This solution was spun in a centrifuge (Component-R, Hanil, Republic of Korea) having a low-acceleration spinning function. The solution was centrifuged at 4° C for 35 minutes under a centrifugal force of 4,500 g. The precipitate forms three distinctive layers after centrifugation. A small amount of a bottom layer contains cells and insoluble and/or denatured proteins, and the largest amount of an intermediate layer and a small amount of a top layer contains both the surfactant lipids and surfactant proteins whish are required in this invention. The intermediate and top layers of the precipitate was collected together and proceeded to the organic solvent extraction to obtain a di-saturated phospholipid fraction.

(3) Primary Organic Solvent Extraction

A 2-fold volume of distilled water was added to the mixture of the surface-active protein and the surfactant lipid prepared in the previous step, and the then mixture was suspended. A mixed solvent (2:1 volumetric ratio) of chloroform and methanol was added to the sample at the same volume, and shaken at 30° C for 30 minutes. The sample was centrifuged for 15 minutes under a centrifugal force of 1,000 g, and then the organic solvent layer was collected for the further isolation procedure.

Figure 1:
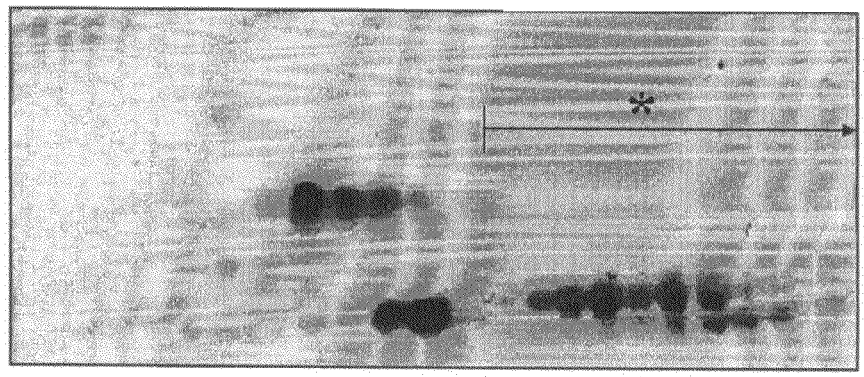
FIG. 1 is a diagram showing that total lipids obtained from animal lung are visualized using TLC.

(4) Extraction of the Di-saturated Phospholipid Fraction Using Silica Column Chromatography A solvent was evaporated from the sample obtained by the primary organic solvent extraction using a rotary vacuum evaporator (Eyela, Japan) and then the sample was re-dissolved in chloroform. The sample was loaded into a column having a diameter to height ratio of 1:5, filled with silica (Merck, 230-400 mesh). The silica column was pre-washed with pure chloroform before the application of the sample onto the column. To get rid of cholesterol and the surface-active proteins that are soluble in the organic solvent, especially in acetone and in order to obtain a di-saturated phospholipids fraction, the solvent systems were employed in the following order. After the application of the sample in chloroform: pure chloroform—pure acetone—pure chloroform—a mixed solvent of chloroform:methanol (9:1 volumetric ratio)—a mixed solvent of chloroform:methanol (4:1 volumetric ratio) and, a mixed solvent chloroform:methanol:water (8:6:1 volumetric ratio) as a final solvent. The organic solvent-soluble surface-active proteins and hydrophobic peptides was eluted in the early stage of the column work when the column washed with the solvents of pure acetone and pure chloroform, and a fraction of di-saturated phospholipids, which is required for the present invention, was eluted with the last solvent system. Each of the phospholipid components of the fractions was identified using 2D-TLC (2-dimensional thin film chromatography) using the standard lipids (commercially available from Sigma) (FIG. 1). Main components of the extracted di-saturated phospholipids were dipalmitoylphosphatidylcholine and dipalmitoylphosphatidylinositol.

(5) Post-treatment Process of the Extracted Di-saturated Phospholipid Fraction

The final sample extracted from the column was passed through a 3-layer Whatman Filterpaper No. 1, and then the solvent was removed using a rotary vacuum evaporator. Pure ethanol was added to the solvent-free sample, and then filtered using a PVDF (polyvinylidene fluoride, 0.22 μm pore-size, Millipore) filter. Ethanol was evaporated again using an evaporator. Washing the sample with ethanol was carried out 2 times. A trace amount of the remaining ethanol was removed using a freeze-drier. A powder form of the di-saturated phospholipids was stored at −70° C in an air-tight storage container filled with nitrogen gas.

Example 2

Extraction of the Di-saturated Phospholipid Fraction from Bronchial Alveolar Lavage of Cattle The method of the steps (1) to (5) described in Example 1 was repeated to obtain the di-saturated phospholipid fraction from a bronchial alveolar lavage of cattle, except that a cattle was used instead of a pig.

Example 3

Method for Obtaining the Di-saturated Phospholipid Fraction from a Lung Tissue Homogenate of Healthy Pig (1) Primary Homogenization of the Animal Lung Tissue 150 g of a lung tissue taken from a healthy pig was cut into a size of approximately 2 cm×2 cm. 700 ml of a cooled osmotic-saline solution containing 3 mM divalent positive ions (calcium chloride) was added to the diced lung pieces, and then homogenized with a metal-blade blender. Homogenization was carried out 6 times at a low rotational speed for 20 seconds each. During the homogenization, the blander was often cooled using an ice-water bath so as to prevent temperature from being increased. The lung tissues were cut at about a bean size without being completely homogenized at an early stage.

(2) A Method for Removing Serum From a Primary Homogenate Without a Loss of Surfactant Lipids The primary homogenate prepared thus was kept for 1 hour in an ice-water bath to allow serum to easily exude from the homogenized tissue having a large surface area, and simultaneously to allow the surfactant components to be aggregated in the presence of divalent ions (calcium ion, 3 mM). The homogenate was kept for 1 hour, and then centrifuged at 4° C for 40 minutes under a centrifugal force of 4,500 g using a centrifuge having a low-acceleration spinning function. A solution containing serum except a precipitate and floating matters (some small bean sizes of the lung tissue that is not completely homogenized floats because it includes the air in them) was removed after centrifugation.

(3) Secondary Homogenization of the Lung Tissue and the Precipitation of the Surfactant Lipids 500 ml of a 75 mM sodium chloride solution (a half concentration of a saline solution) containing 5 mM divalent positive ion (calcium ion) was added to the serum-free primary lung tissue homogenate, and then the tissue was minutely homogenized with a metal-blade blender. In this procedure, a hypotonic solution was employed to obtain easily multilamellar structures that have function as a reservoir of the surfactant lipids existing inside Type II epidermal cells in alveoli. Homogenization was carried out 6 to 8 times at a high rotational speed for 40 seconds each, and the blander was often cooled using an ice-water bath so as to prevent temperature from being increased during the homogenization procedure. The secondarily homogenized sample was kept at 4° C for 1 hour to prevent the blood coagulation proteins from being coagulated and at the same time, to allow the SP-A protein to aggregate with the surfactant lipids in the presence of calcium ions. The sample was centrifuged at 4° C for 40 minutes under a centrifugal force of 4,500 g using a centrifuge having a low-acceleration spinning function. The sample forms two distinctive layers that are clearly different in colors and textures after centrifugation. A supernatant of the precipitate layer was separately taken and subject to an organic solvent extraction procedure so as to fractionate the di-saturated phospholipids. A certain amount of the surfactant lipids integrated into the bottom layer in the centrifuge tubes could be extracted as the saline solution containing 5 mM calcium ions was added to the bottom layer again and suspended it again, and then centrifuged in the same manner as described above. The reformed top layer of the precipitate was collected and combined with the sample prepared previously, and then subject to the organic solvent extraction procedure.

(4) A method for obtaining the di-saturated phospholipid fraction

The method of the steps (3) to (5) described in Example 1 was repeated to obtain a di-saturated phospholipid fraction from the lung tissue homogenate.

Example 4

A Method for Obtaining a Di-saturated Phospholipid Fraction from a Lung Tissue Homogenate of Healthy Cattle The method described in Example 3 was repeated to obtain the di-saturated phospholipid fraction from a bronchial alveolar lavage of cattle, except that a cattle was used instead of a pig.

Experimental Example 1

Animal Experiment 1-1. Induction of the Exudation of the Serum Proteins in Animal Lung Corn oil (commercially available from Sigma Co.) and a saline solution were sterilized, respectively, using an autoclave. 500 µl (microliter) of the corn oil and 1500 µl of the saline solution were mixed, and then vortexed very vigorously to give a homogeneous suspension. The suspension was intratracheally administered to the lungs of grown-up Sprague-Dawley rats to induce the exudation of the serum proteins in the lung. In order to study a placebo effect, only the sterile saline solution was intratracheally administered to the control rats. 2 weeks after application, the groups of rats were anesthetized using an anesthetic Ketamine (Yuhan Co. Ltd., republic of Korea), and then immediately euthanized using carbon dioxide gas. Lung was taken out right after the experimental animal was killed, and the lung was lavaged with total 50 ml of a saline solution (containing 3 mM calcium chloride) to collect a bronchial alveolar lavage in each animal.

1-2. Test of an Effect on the Suppression or Reduction of the Serum Protein Exudation and the Component of the Composition Applied The exudation of the serum proteins was induced in animals in the same method described above, and then the compositions containing the di-saturated phospholipid fraction prepared in Examples 1 to 4 were administered intratracheally 1 week after the induction of the serum protein exudation procedure. The lung extraction and bronchial alveolar lavage from the experimental animals were carried out 1 week after the compositions were administered intratracheally.

The composition applied to the rats to suppress or to reduce the exudation of the serum proteins in lung was a concentration of 30 mg/ml of di-saturated phospholipids, 1.5 mM calcium chloride, 7.5 mM citrate (citrate trisodium salt) and 125 mM sodium chloride, and pH of the solution was set to 6.0. The solution was vigorously vortexed to form a homogeneous suspension before it was administered to the animal.

1-3. Analysis of the Induction and Suppression of the Exudation of Serum Proteins in the Tested Animals (1) Preparation of the Samples from Each Experimental Animals The bronchial alveolar lavages obtained from each experimental animal group were centrifuged at 4° C for 30 minutes under a centrifugal force of 4,500 g using a centrifuge having a low-acceleration spinning function. Only a layer of the surfactant, aggregated in the presence of divalent ion (calcium ion) with SP-A, was collected from the precipitate. Approximately 3-fold volume of a saline solution (including 3 mM calcium chloride) was added to the collected precipitate and the precipitate was suspended again. The suspension was centrifuged under the same centrifugal force to form a pellet. The washing procedure described above was repeated twice to clean up the pellet using the same solution. A suspension of the final precipitate was divided into 1 ml miniature centrifuge tubes, and the volume of the precipitate was adjusted to 200 μl.

1 ml of 10 mM Tris buffered saline (pH 7.4, 10 mM Tris-HCl, 140 mM NaCl) containing 10 mM EDTA (ethylenediamineteteraacetic acid) was added to 200 μl of the surfactant precipitate described above, and the precipitate was then suspended in the solution. An zwitter-ionic detergent CHAPS (Amresco, USA) was added to the solution drop by drop with gentle shaking until the suspension was solubilized by CHAPS. In order to solubilize the sample, a concentration of a 10% (w/v, approximately 162 mM) CHAPS stock solution was employed and the final concentration of CHAPS in the sample was about 65 mM.

Figure 2:
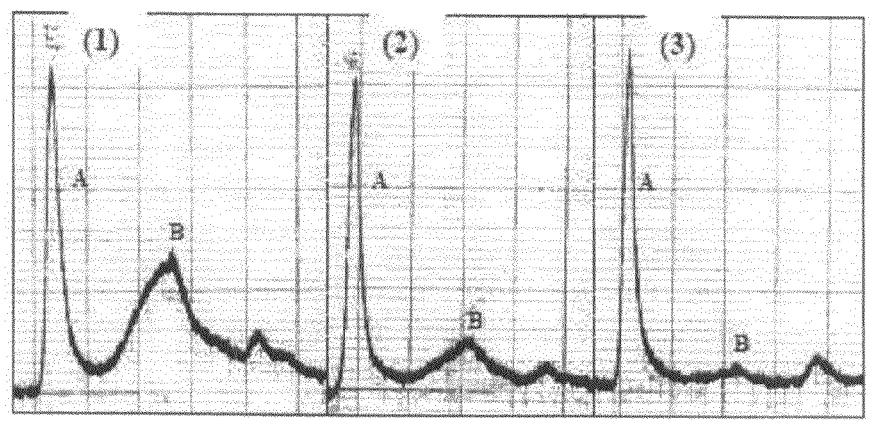
FIG. 2 is a chromatographic diagram showing the results of the protein elution pattern from each column chromatography work after the exudation of the serum proteins is induced in rat lung and then suppressed by a composition.

(2) Analysis 1 ml of the samples were taken from each sample (2 ml) prepared in the procedure described above, and applied to a chromatography column packed with Sephacry S-400HR (1.5 cm×20 cm, Amersham Bioscience) resin to analyze the elution pattern of the proteins. The size-exclusion chromatography was carried out using GradiFrac (Pharmacia). At this time, the buffer solution used in the chromatography work as a running buffer was a 10 mM Tris buffer solution (pH 7.4) including 5 mM EDTA, 1 mM CHAPS and 140 mM NaCl. An exudation level of the serum proteins and a suppression level of the proteins were determined, respectively, by comparing a size (quantity) of an peak containing SP-A around a molecular weight of 700 kDa with a size of a peak containing albumin around a molecular weight of 70 kDa from a UV absorption graph of the proteins eluted from the column (see FIG. 2).

1-4. Animal Experiment Results

From the graph of the protein elution patterns of the samples obtained from the group of the tested rats in which the exudation of the serum proteins was induced, the samples of the rats in which exudation of serum proteins was suppressed by the administration of the composition, the samples obtained from the rats into which only a saline solution was administered, and the sample obtained from the untreated control rats, the ratios of the protein peak sizes around a molecular weight of 700 kDa to the protein peak sizes around a molecular weight of 70 kDa were calculated respectively. The ratios of two peak sizes (quantity) obtained from the groups of rats were listed in the following Table 1.

From and the obtained results shown in the Table 1, it was discovered that the compositions containing the di-saturated phospholipid fraction as a main component reduces, extracted from the bronchial alveolar lavage and from the lung homogenate of the healthy animal, the serum protein exudation in the tested rats was reduced. A peak size of the proteins containing albumin as a major protein was reduced by approximately 50% when the composition was administered intratracheally only one time, compared to the results of the serum protein exudation-induced rats. Such a reduced amount showed in Table 1 represents a value calculated simply from the criterion set in the size-exclusion chromatography. However, the actual reduced amount of the exudates is highly larger than the calculated value shown in Table 1. The reason is that 2-3 ml of a precipitate (volume/head) is generally obtained on average when the bronchial alveolar lavage samples are obtained from normal rats, but the amount of precipitate obtained from the serum protein exudation-induced rats were 3 to 5 times larger than that of the normal rats although a quantity of the precipitate may be widely varied depending on subjects. However, the amounts of the precipitates from the rats in which the serum protein exudation were suppressed by the composition of the present invention were almost the same or more than, at most, about 2 times those of the precipitates obtained from the control rats. That is, it was shown that the composition of the present invention significantly reduced a total amount of the precipitates, when they were compared to those obtained from the serum protein exudation-induced rats. However, these values are not shown in here quantitatively since the quantities of the precipitates obtainable from the tested rats may be greatly varied by the experimental factors such as the experiment temperature, the compliancy of lung tissues, examiner's dexterity, etc. Therefore, the reductions of the serum proteins shown in FIG. 2 and Table 1 did not exhibit the total amount of the proteins. They only show the ratios between the peak sizes containing SP-A and the peak sizes containing serum albumins as major protein the fraction. As the total amounts of the serum proteins reduced by the composition of the present invention (see B of FIG. 2(2)) are measured, it might be found that the reduced levels are very significant in its effect.

From the results shown above, it was found that the most ideal composition of di-saturated phospholipids for suppressing or reducing the serum protein exudation was the one isolated from the bronchial alveolar lavage of healthy animal. However, the di-saturated phospholipid fraction obtained

TABLE 1

|  | Ratio of Protein peak around 700 kDa/ Protein peak around 70 kDa |
| --- | --- |
| Serum protein exudation-induced group | 0.8 |
|  | 1.1 |
|  | 1.4 |
| Composition of Example 1 or 2 administrated | 2.0 |
|  | 2.3 |
| Composition of Example 3 or 4 administrated | 1.9 |
|  | 1.9 |
|  | 2.1 |
|  | 2.3 |
| Only saline-administered control group | 4.4 |
|  | 5.7 |
| Control group (untreated rat) | 4.2 |
|  | 4.3 |
|  | 4.8 | from the de-blooded lung tissue homogenate also exhibited the almost same suppression level of the exudation of the serum proteins in the results Experimental Example 2

Test on Volunteers with Atopic Skin Disease 2-1. Application of Composition Used in Skin (1) Composition The di-saturated phospholipid fraction obtained from the pig lung homogenization method exploiting an aggregation phenomenon of the surfactant by divalent positive ion (calcium ion) and filtered through a PVDF (polyvinylidenefluoride, 0.2 μm pore-size, Millipore) filter having a pore size of 0.22 μm was used in the test. The fraction was freeze-dried. A certain concentration of the dried di-saturated phospholipids was emulsified in iso-osmotic saline and then autoclaved. A calcium chloride stock solution, a citrate (citrate trisodium salt) stock solution and glycerol were also autoclaved, respectively. Each sterilized component (solution) was mixed under an aseptic condition to a concentration of 15 mg/ml of di-saturated phospholipids, 1.5 mM of calcium ions, 7.5 mM of citrate (citrate trisodium salt) and 10% (volume/volume ratio) glycerol to pH 6.0. Glycerol was added at 10% of the total concentration to give viscosity (or stickiness) to the solution so that the di-saturated phospholipids can be easily spread on skin with a mechanical force during the application on the skin. The mixed components were vigorously vortexed to form a homogeneous suspension, and then used hereinafter.

(2) Application

The application on skin was carried out by falling a drop (approximately 30 μl) of the solution (described above) on every 2 cm×2 cm of the ailing skin area and then by rubbing the solution very softly until it is absorbed completely to the skin. It was recommended that the solution be applied at least 2 times daily. It was also recommended that cosmetics or soaps with strong scent, which may contain the chemicals having an aromatic ring(s) be not used during the application period of the composition.

2-2-1. Experiment Results on Primary Volunteers (Observation with the Naked Eye)

The tests on volunteers were carried on 15 skin sites of 8 volunteers (5 to 40 years old, average age of 33 years old, 4 males and 4 females) suffering from atopic skin diseases. The application of the composition on the skin was carried out for a period of 2 to 4 weeks in which the period was determined by both the severity and the improvement of skin conditions. It was found that, during the period of the application, the symptoms of the atopic skin diseases were improved in all of the test volunteers to the extent that it is difficult to distinguish the boundaries of the previous diseased skin area.

Figure 3:
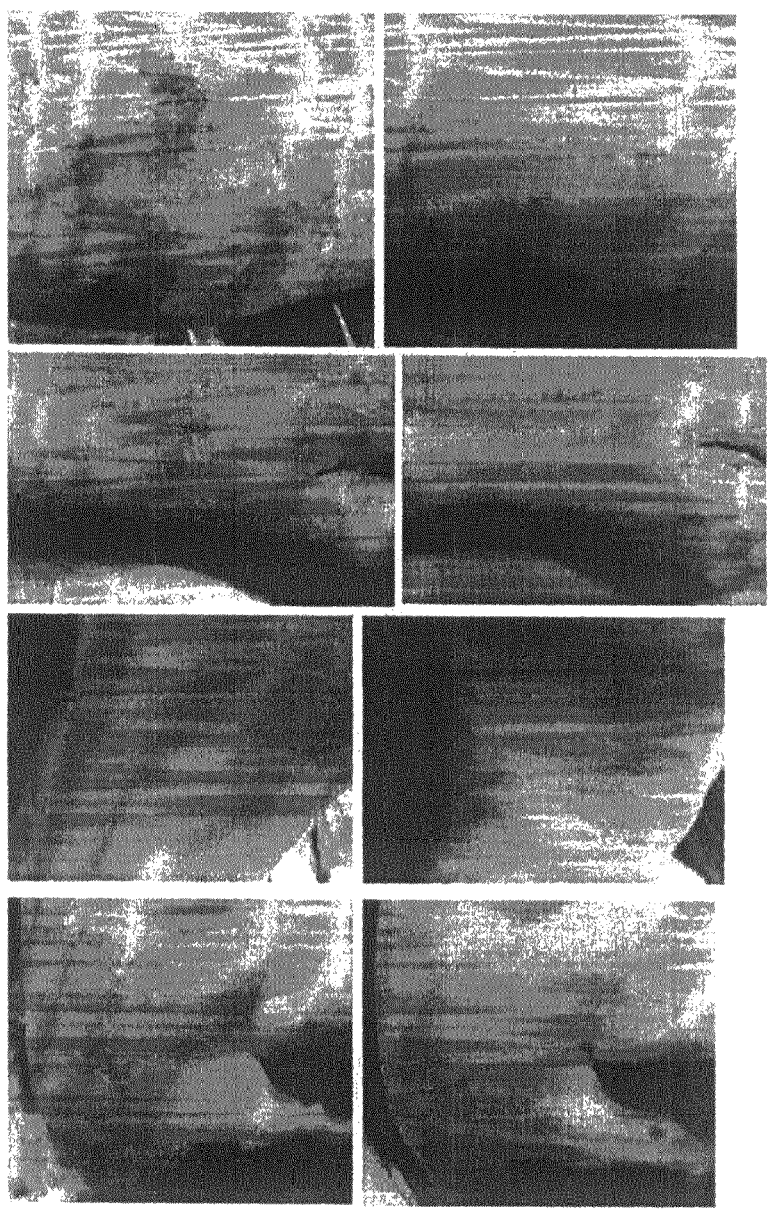
FIG. 3 is a photograph showing the results after the composition was applied to the atopic skin diseases (2 to 4 weeks). The lefts parts of the photograph show the condition of the skin before the application of the composition. The right parts of the photograph show the results after the application of the composition. The application of the composition was carried out for the period of 2 to 4 weeks, the top of the photograph shows a patient suffering from atopic eczema, the second photograph from the top shows a patient suffering from atopic dermatitis including skin ulcer, the third photograph from the top shows a patient suffering from atopic erythema, and the bottom of the photograph shows a patient suffering from atopic dermatitis.
Figure 4:
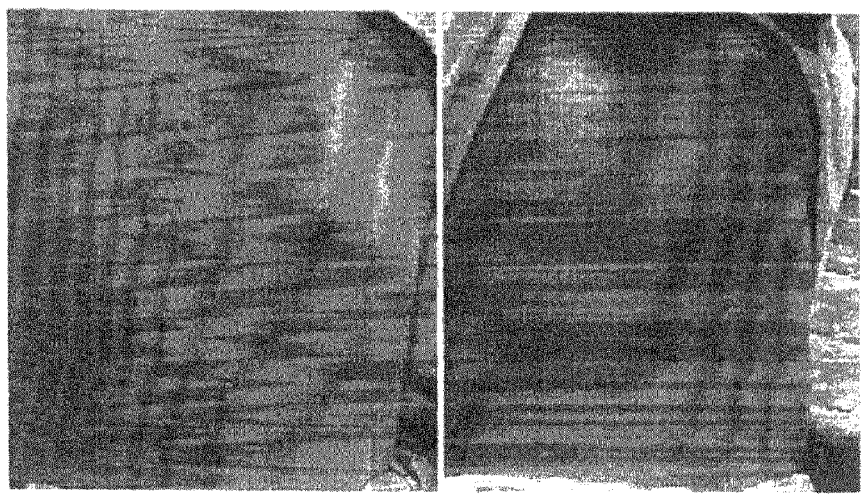
FIG. 4 is a photograph showing the result before/after the composition was applied. These result shows photographs taken before the application of the composition to an atopic skin disease developed in the back of a 6-year-old female (left) and after application of the composition to the atopic skin disease for 4 weeks (right).
Figure 5:
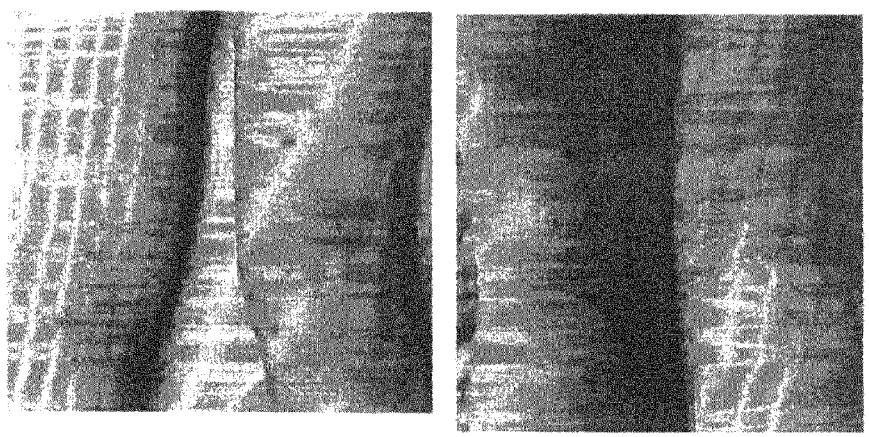
FIG. 5 is a photograph showing the result before/after the composition was applied. These result shows photographs taken before application of the composition to an atopic skin dermatitis, including skin ulcer, developed in a popliteal region of the knee of a 6-year-old female (left) and after the application of the composition to the atopic skin dermatitis for 5 weeks (right).
Figure 6:
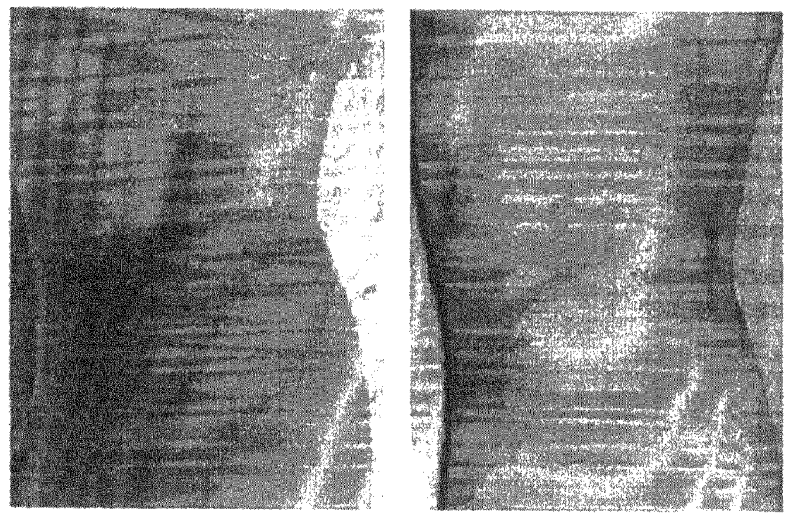
FIG. 6 is a photograph showing the result before/after the composition was applied. These result shows photographs taken before the application of the composition to a common atopic skin disease developed in a popliteal region of the knee of a 16-year-old female (left) and after the application of the composition to the atopic skin disease for 3 weeks (right).
Figure 7:
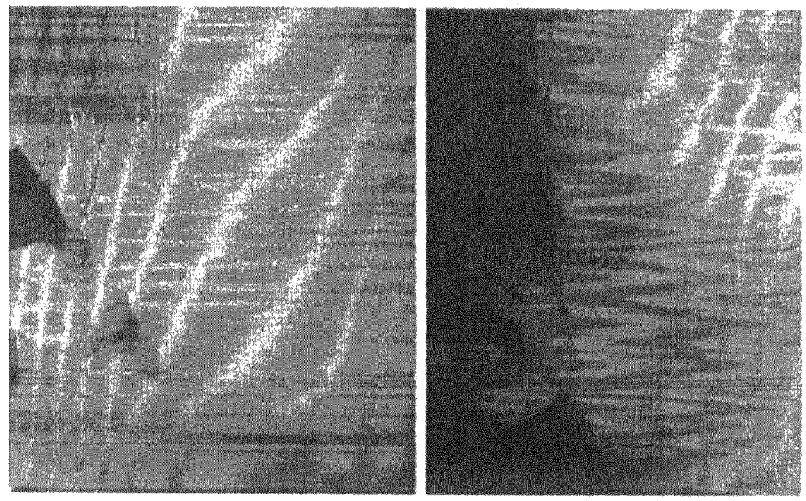
FIG. 7 is a photograph showing the result before/after the composition was applied. These result shows photographs taken before the application of the composition to an early-stage atopic skin disease developed in the face of a 10-month-old female (left) and after the application of the composition to the atopic skin disease for 3 weeks (right).

It was observed that skin crusts, formed since the skin exudates are dried due to the atopic skin diseases, are not formed again in the skin surface about 3 days after the application of the composition. In the case of the volunteers with the atopic erythema, the symptom disappeared so that the rim of the affected skin area by atopic skin disease could not be distinguished 1 week after the application of the composition. It was confirmed that the wounds were completely recovered 3.5 weeks (approximately 25 days) after the application of the composition in the case of the patients having complications of skin gangrene (skin ulcer) (see FIG. 3).

2-2-2. Experiment Results on Secondary Volunteers (Observation with the Naked Eye)

Another tests on volunteers were carried on 27 volunteers (0.8 to 42 years old, average age of 23.4 years old, 13 males and 14 females) suffering from atopic skin diseases.

The application of the composition on the skin was carried out for a period of 2 to 5 weeks. The symptoms of the atopic skin diseases were improved in 25 volunteers except 5 volunteers to the extent that it is difficult to distinguish the boundaries of the originally diseased skin area. 2 patients who had a complication of atopic skin disease and severe acne symptom on the face and the back, respectively, did not show the significant improvement of the condition. 3 volunteers who had a very thick cornification of skin as a consequence of the very long atopic skin diseases sufferings showed the slight improvement of the skin condition during the period of the application. 3 out of 25 volunteers whose symptoms were clearly improved had to be treated with an antibacterial ointment during the application of the composition because a skin infection was observed and the patients could not overcome the infection for themselves. The photographs showing the results of the skin condition improvement are shown in FIGS. 4 to 7.

Industrial Applicability

As described above, the composition containing the di-saturated phospholipids, the present invention has a significant effect in treating or relieving the symptoms of atopic diseases, etc. caused by the exudation of the serum proteins in skin and mucosa.

What is claimed is:

1. A homogeneous composition for treating and relieving a disease showing the exudation of serum proteins, comprising di-saturated phospholipids, calcium ions, and an organic acid(s) containing carboxyl group(s) selected from the group consisting of succinic acid and citric acid,
wherein said di-saturated phospholipids are present in the composition at a concentration of 1-700 mg/ml; said calcium ions are present in the composition at a concentration of 0.5-5 mM; and said organic acid(s) containing carboxyl group(s) is present in the composition at a concentration of 2-22.5 mM.

2. The composition according to claim 1, wherein the di-saturated phospholipids are extracted from animals.

3. The composition according to claim 1, wherein the di-saturated phospholipids are extracted from cattle and pig.

4. The composition according to claim 2, wherein the di-saturated phospholipids are extracted from bronchial alveolar lavage, lung tissue homogenate or a mixture thereof.

5. The composition according to claim 1, wherein the di-saturated phospholipids comprise dipalmitoylphosphatidylcholine, dipalmitoylphosphatidylinositol or a mixture thereof as major constituents.

6. The composition according to claim 1, further comprising glycerol.

7. A method for treating and relieving the diseases showing the exudation of the serum proteins are selected from the group consisting of atopic dermatitis, atopic eczema, skin pruritus, atopic nasitis, atopic erythema or erythroderma, and contact dermatitis, asthma, and chronic obstructive pulmonary disease, the method comprising administering the composition defined in claim 1 to a patient in need thereof.

8. The composition according to claim 1, wherein the di-saturated phospholipids are present at a concentration of 15 to 30 mg/ml.

9. The composition according to claim 3, wherein the di-saturated phospholipids are extracted from bronchial alveolar lavage, lung tissue homogenate or a mixture thereof.

10. The composition according to claim 2, wherein the di-saturated phospholipids include dipalmitoylphosphatidylcholine, dipalmitoylphosphatidylinositol or a mixture thereof.

11. The composition according to claim 3, wherein the di-saturated phospholipids include dipalmitoylphosphatidylcholine, dipalmitoylphosphatidylinositol or a mixture thereof.

12. The composition according to claim 1, wherein the disease showing the exudation of the serum proteins is selected from the group consisting of atopic dermatitis, atopic eczema, skin pruritus, atopic nasitis, atopic erythema or erythroderma, and contact dermatitis, asthma, and chronic obstructive pulmonary disease.

13. The composition according to claim 1, wherein said calcium ions are present in the composition at a concentration of 0.5-2.5 mM; wherein said organic acid containing a carboxyl group is present in the composition at a concentration of 2-12.5 mM.

14. A composition comprising di-saturated phospholipids, calcium ions, and an organic acid(s) containing carboxyl group(s) selected from the group consisting of succinic acid and citric acid, wherein said di-saturated phospholipids are present in the composition at a concentration of 1-700 mg/ml; said calcium ions are present in the composition at a concentration of 0.5-5 mM; and said organic acid containing a carboxyl group is present in the composition at a concentration of 2-22.5 mM for preventing said di-saturated phospholipids from being aggregated by said calcium ions.

15. The composition according to claim 14, wherein said calcium ions are present in the composition at a concentration of 0.5-2.5 mM; wherein said organic acid containing a carboxyl group is present in the composition at a concentration of 2-12.5 mM.

16. The composition according to claim 1, wherein said di-saturated phospholipids are present in the composition at a concentration of 1-30 mg/ml.

17. The composition according to claim 1, wherein said di-saturated phospholipids are present in the composition at a concentration of 1-15 mg/ml.

18. A homogeneous composition for treating and relieving a disease showing the exudation of serum proteins, comprising di-saturated phospholipids, calcium ions, and an organic acid(s) containing carboxyl group(s) selected from the group consisting of succinic acid and citric acid,
   wherein said di-saturated phospholipids are present in the composition at a concentration of 1-700 mg/ml; wherein said calcium ions are present in the composition at a concentration of 0.5-5 mM; and wherein said organic acid(s) containing carboxyl group(s) is present in the composition at a concentration of 2-22.5 mM;
   wherein the composition reduces the exudation of the serum proteins in a serum protein-induced rat following intratracheal administration such that a ratio of a protein peak around 700 kDa to a protein peak around 70 kDa in the serum protein exudation-induced rat treated with the composition ranges from about 1.9 to about 2.3 based on the size-exclusion chromatography using a 10 mM Tris buffer solution including 5 mM EDTA, 1 mM CHAPS and 140 mM NaCl, wherein the buffer solution has a pH of 7.4.

19. The composition according to claim 18, wherein the protein peak around 700 kDa comprises a surfactant protein, and wherein the protein peak around 70 kDa comprises serum albumin.

* * * * *